United States Patent [19]

Loop

[11] Patent Number: 4,637,377
[45] Date of Patent: Jan. 20, 1987

[54] PILLOW OR SUPPORT MEMBER FOR SURGICAL USE

[76] Inventor: Floyd D. Loop, 1 Bratenahl Pl., #1206, Cleveland, Ohio 44108

[21] Appl. No.: 778,544

[22] Filed: Sep. 20, 1985

[51] Int. Cl.⁴ .............................................. A61B 19/00
[52] U.S. Cl. .................................... 128/1 R; 604/346; 604/356
[58] Field of Search ............... 128/1 R; 604/346, 356; 5/431, 433, 434, 435, 436, 441, 442, 446, 450

[56] References Cited

U.S. PATENT DOCUMENTS

| | | | |
|---|---|---|---|
| 1,382,531 | 6/1921 | Newborn | 5/441 |
| 1,491,146 | 4/1924 | Larson . | |
| 2,139,803 | 12/1938 | Cavicchi | 5/468 |
| 2,522,120 | 9/1950 | Kaskey et al. | 5/337 |
| 3,308,491 | 3/1967 | Spence | 5/348 |
| 3,378,864 | 4/1968 | Cornes | 9/11 |
| 3,421,163 | 1/1969 | Stoughton | 5/450 |
| 3,426,372 | 2/1969 | Enelow | 5/434 |
| 3,968,530 | 7/1976 | Dyson | 5/338 |
| 3,983,863 | 10/1976 | Janke et al. | 128/1 R |

Primary Examiner—C. Fred Rosenbaum
Assistant Examiner—J. L. Kruter
Attorney, Agent, or Firm—Body, Vickers & Daniels

[57] ABSTRACT

A surgical pillow for supporting the heart or other body organs of a patient during surgical operations thereon is formed of an inner body member or filling which is readily deformable by external forces applied to the pillow, as by the patient's organ pressed thereagainst, so as to accommodate itself to the shape of such organ, and which is completely encased within an outer envelope of a thin, flaccid sheet of a synthetic plastic material impervious to air and liquid and non-absorbent of human blood and the outer surface of which is preferably of a character preventing slippage of the body organ thereon without causing irritation or contraction of the supported organ. The inner body member or filling may comprise an aggregate of particulate synthetic plastic foam material such as expanded plastic kernels or beads such as so-called micro-balloons, or it may be formed of soft, spongy, finely cellular material such as sponge rubber or a foamed spongy synthetic plastic such as polyurethane foam. The outer envelope may have a small vent opening in its side wall to permit release of entrapped air or gas from the envelope on compression of the pillow.

3 Claims, 7 Drawing Figures

PILLOW OR SUPPORT MEMBER FOR SURGICAL USE

BACKGROUND OF THE INVENTION

This invention relates to a surgical pillow for supporting the heart or other body organs of a patient during surgical operations performed thereon, such as open heart surgery for example, and to a method of performing such operations.

Open heart surgery such as bypass operations on the circumflex artery system are especially difficult because of the inaccessibility of the field of operation on the heart and the difficulty of maintaining the heart in place in a steady position.

In the performance of such open heart operations heretofore, it has been common practice to support the heart by means of hygienic cotton gauze during the progress of the surgical operation. At the conclusion of the operation, the patient's blood lost during the course of the operation is pumped from the patient's chest cavity, and also rinsed out of the gauze support which has absorbed some of the lost blood, and after proper cleansing is then reused by reinjection into the patient's blood circulation system. With this improved operating procedure, the amount of blood required to be transfused to the patient in open heart surgery was reduced from the previous average eight to eleven pints to as little as two pints or so. However, in employing a gauze support for the patient's heart as referred to above, it is quite difficult to keep the heart in a steady position during the course of the bypass operation.

Other forms of support for a patient's heart during open heart surgery have been proposed heretofore. Thus, a fishnet type support of rectangular outline and formed of fine inelastic strands has been previously proposed but found unsatisfactory. The fine inelastic strands of such a fishnet support impinge on the coronary arteries, such as might stop all coronary circulation and possibly cause some additional myocardial damage.

U.S. Pat. No. 3,983,863 to Janke et al., discloses a heart support which is described as being an improvement over the above-mentioned fishnet support. The heart support shown in this patent is formed of a network or open mesh of crossing flat cloth tapes having a heart shaped outline and provided with stretchable cloth end tapes for positioning around the heart while the apex of the left ventricle thereof is temporarily lifted from the pericardial cavity of the patient, and then tying the end tapes together, after the heart is lowered back into the pericardial cavity, to secure the support to the heart. The broad end of the heart support is then pulled upward to expose the circumflex artery system of the heart and clamped to the surgical drapes overlying the patient. The so positioned heart support is stated to then hold the heart in steady position for bypass operations on the circumflex coronary artery of the patient. However, the retrieval and reuse of the patient's blood lost through absorption by the cloth tapes of such a heart support necessitates the time consuming operations of rinsing the absorbed blood out of the support and cleansing such retrieved blood before returing it to the patient's circulatory system.

Support pillows adapted for entirely different uses than as a support for a patient's heart or other body organs are, of course, well known in themselves. Thus, U.S. Pat. No. 1,491,146, Larson, discloses a head rest pillow consisting of a concavely dished outer envelope of pliant material such as india rubber or textile fabric, which may be either inflatable with air under pressure through a subsequently closed nipple in the envelope wall or which may be filled with a compressible padding material such as sponge rubber. U.S. Pat. No. 2,522,120, Kaskey et al., discloses a head, or neck, or back rest pillow shaped to conform to the contour of the body portion to be rested and formed of an outer fabric case or covering filled with a suitable cushion filler such as foam or sponge rubber or Kapok molded to the desired shape, or containing an inflatable rubber or plastic bladder. U.S. Pat. No. 3,308,491, Spence, discloses a body support cushion for a chair seat, bed pad, or the like, comprised of a thin, elastic cover of gum or latex sheet material filled with a gel-like substance having a jelly-like consistency, such as an organosiloxane gel. U.S. Pat. No. 3,378,864, Cornes, discloses a self-inflating buoyant device such as a life raft, sleeping mattress, cushion, bumper or protective device, which is comprised of a preformed inner body member of a polyurethane synthetic cellular aeriferous material encased in an envelope of vinyl or plastic coated nylon having an orifice with a removable closure cap in the envelope wall for permitting selfinflation of the device. U.S. Pat. No. 3,968,530, Dyson, discloses an external body support pad or mattress, such as a sacral pad or heel pad, comprised of an inner filling of a mixture of a gel or viscous fluid and fine sawdust or hollow beads of silica and organic silicates or polystyrene, enclosed within a flexible fluid-impermeable envelope of PVC sheet which, in turn, is enclosed within an outer cover of open weave cotton material and a second outer cover of polyester-cotton fabric. All of the support pillows shown in the above patents and adapted for other useful purposes are, however, unsatisfactory for one reason or another for use as a surgical support pillow for body organs such as a patient's heart during surgical operations thereon. They would not provide the desired organ supporting action and other advantages provided by the surgical support pillow disclosed herein by applicant.

SUMMARY OF THE INVENTION

The present invention contemplates a new and improved surgical pillow which overcomes all of the above referred to problems and others and provides a pillow or support member of simple and economical form for effectively accommodating itself to the shape of and supporting in steady position a patient's heart or other body organ during the course of open heart or other surgery, and substantially reduces the amount of transfused blood required during such surgery.

Briefly stated, in accordance with one aspect of the invention, a surgical pillow or support member is provided having an inner body or filling which is readily deformable by external forces applied to the pillow, as by the patient's organ pressed thereagainst, so as to readily accommodate itself to the shape of the supported surface of the organ, and which is completely encased within an outer envelope of a thin, flaccid sheet of a synthetic plastic material impervious to liquid and air and nonabsorbtive of human blood and the outer surface of which is preferably of a character preventing slippage of the body organ thereon.

In accordance with a further aspect of the invention, the envelope of the surgical pillow is preferably provided with a small vent opening in the side wall thereof to permit ready outflow of air from the envelope on compression of the pillow as well as inflow of air on decompression of the pillow.

The principal object of the invention is to provide a surgical pillow or support member for effectively supporting a patient's heart or other body organ in steady position during the course of open heart or other surgical operations thereon and which substantially reduces the amount of blood lost and required to be transfused to the patient during such operations.

Another object of the invention is to provide a surgical pillow of the above-mentioned character which will readily conform to the contour of and cradle the patient's heart or other body organ under the pressure thereof, when supported on the pillow, to keep the body organ in steady position and restrained from sliding on the pillow.

Still another object of the invention is to provide a surgical pillow of the above-described character which is nonabsorptive of the patient's blood and not apt to impinge on the coronary arteries of the patient during open heart surgery to possibly stop coronary circulation or cause additional myocardial damage.

A further object of the invention is to provide a surgical pillow of the above-described character which is of inexpensive and light weight construction is easily handled and positionable in place as well as repositionable by the attending surgeon or aides.

Further objects and advantages of the invention will become apparent from the following detailed description of preferred species thereof taken in conjunction with the accompanying drawings.

DESCRIPTION OF THE PREFERRED EMBODIMENTS

Figure 1:
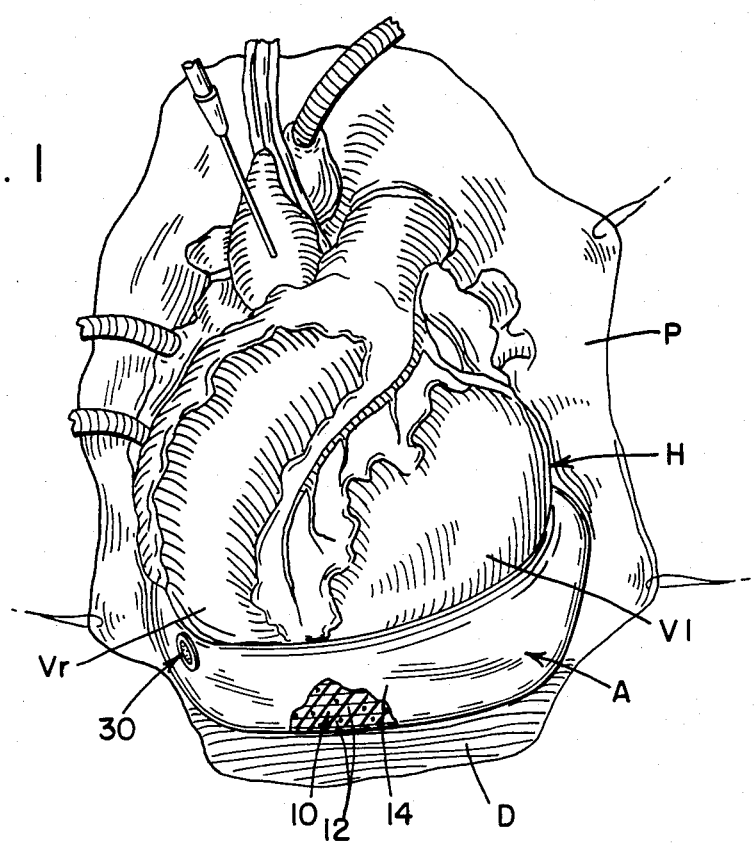
FIG. 1 is an anterior view of the heart of a patient shown supported in place, during open heart surgery, by a surgical pillow or support member comprising the invention.
Figure 2:
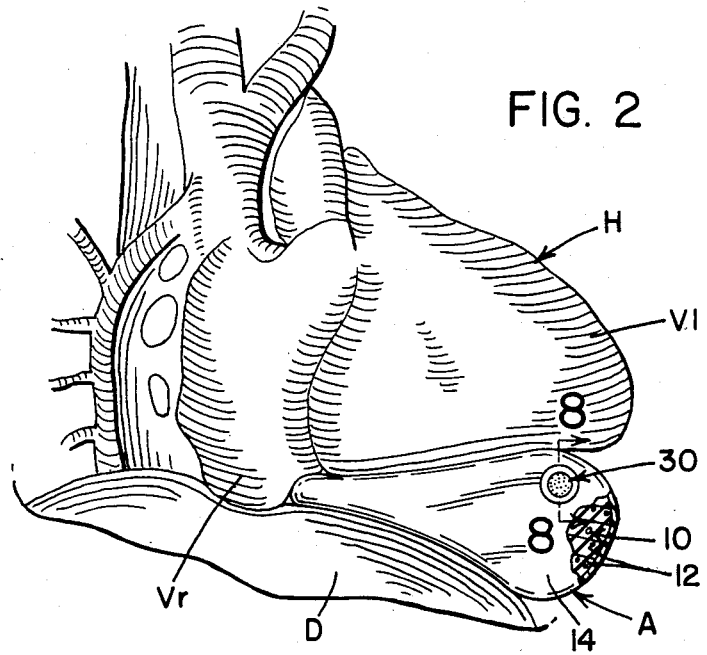
FIG. 2 is a lateral view of the heart of a patient, taken from a different angle from that in FIG. 1, shown supported in place by the surgical pillow comprising the invention.

Referring to the drawings, FIGS. 1 and 2 illustrate a surgical pillow or support member A comprising the invention shown supporting a patient's heart H in steady position during the course of open heart surgery on the patient's circumflex artery system. It should be understood, however, that the surgical pillow can be employed as well to support in steady position during surgery other body organs such as a kidney, for instance, which have a substantial blood flow.

In FIGS. 1 and 2, the patients's heart H is shown exposed within the cut open pericardium or fibrous sac P that normally encloses the heart, and with the left and right ventricles Vl and Vr of the heart supported in steady position by support pillow A which is inserted between the ventricles Vl and Vr of the heart and the patient's diaphragm D located beneath the heart. The steady support afforded to the heart H by the surgical pillow A thus frees the surgeon's assistants for other useful duties to aid the surgeon in performing the bypass operation. The surgical pillow A also may be laterally adjusted, while in its heart supporting position between the patient's heart H and diaphragm D, to effect any limited repositioning and adjusted support of the heart that may be required by the surgeon during the course of the operation.

Figure 5:
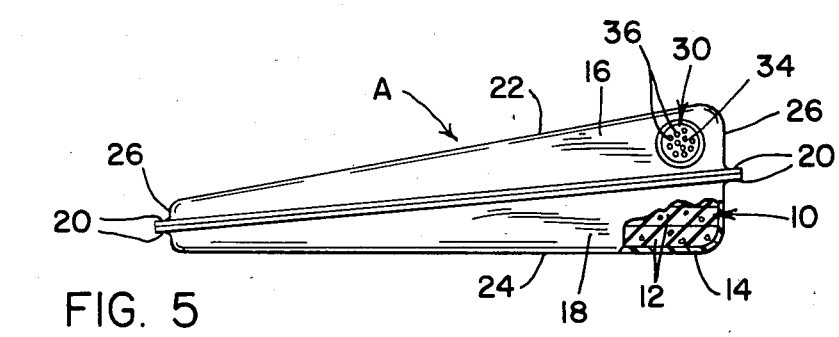
FIG. 5 is a side elevation of a surgical pillow comprising the invention shown partly broken away in section.

As shown more particularly in FIG. 5, the surgical pillow or support member A comprises an inner body or filler 10 which preferably is of light weight and which is readily deformable by external forces applied to the pillow, such as by a patient's heart resting or pressed thereagainst, so as to readily accommodate itself to the shape of the supported heart surface. Suitable materials for the inner body or filler 10 may be an aggregate of particulate synthetic plastic material, foamed or otherwise, e.g., expanded plastic kernels or beads such as those commonly referred to as micro-balloons or hollow spheres. Also suitable for the inner filler 10 are soft, sponge-like, aeriferous, cellular materials such as sponge rubber or a foamed, spongy, synthetic plastic such as spongy polyurethane foam. The commercially known filler materials such as kapok and Kodel are also suitable for use as the inner body or filler 10. The inner body or filler 10 forms the cushion member of the pillow A. The inherent properties of the material of which the member or filler 10 is made are such that the body member, and thus the pillow itself, will readily deform and accommodate itself to the shape of the portion of the patient's heart or other organ which is supported against the pillow. In the case where the body member 10 is made of sponge-like aeriferous cellular material such as sponge rubber or spongy synthetic plastic foam, the inherent properties thereof are such that air will be forced out of, and the body member 10 deformed and contracted in sized and shape when subjected to compression, while air will be drawn back into the pores of the compressed body member to cause it to expand and return to its original size and shape when the compressive forces are removed. In the particular pillow A illustrated in the drawings, the inner body or filler 10 is formed of a plurality of flat layers or pads 12 of the aforementioned soft, compressible, cellular sponge material, which are stacked flatwise one on top another. The individual layers 12 may each have a thickness of around ¼ inch or so, for example. If desired, however, the body member 10 may be formed of a single piece of such cellular sponge material.

The inner body or cushion 10 is completely encased within an outer envelope or casing 14 formed to provide a pad-shaped pillow A when the inner body is in place in the envelope. The envelope or casing 14 is formed of a thin, flaccid, synthetic plastic sheet material which is impervious to liquid and nonabsorptive of human blood and which has a relatively even surface such as will not irritate or cause contraction of the heart or other body organ. A suitable synthetic plastic sheet material for this purpose is polyethylene. Preferably, the outer surface of the envelope 14 is modified to have a somewhat non-slip or non-skid character, such as a fine matte-like surface for instance, so as to prevent slippage of the heart or other body organ thereon during the course of the operation, when the envelope is likely to be covered with the patient's blood. The thin, flaccid sheet casing 14 envelops the inner body or filling 14 as compactly or tightly as possible, but without deforming the body 14 when made of spongy material. In the form of the invention shown in FIG. 5, the plastic sheet casing 14 is formed of two complementary half sections, i.e., an upper section 16 and a lower section 18, which are heat sealed together around their peripheral edges 20 to form the envelope 14. The pillow A thus formed has flat upper and lower surfaces 22 and 24, respectively, of appreciable surface area joined by a relatively narrow side wall 26 extending completely around the pillow.

In the particular form of the invention shown in FIG. 5, the pillow A uniformly increases in thickness from one side edge thereof to the other side edge so that the top and bottom surfaces 22 and 24 of the pillow A correspondingly taper or diverge relative to one another from one side edge to the other side edge of the pillow. For example, relatively thin pillows A could have a thickness of around ¾ inch at the side edge adapted to be positioned posteriorly of the patient's heart and uniformly increasing in thickness to around 1¼ inch at the opposite side edge to be positioned anteriorly of the patient's heart. Relatively thick pillows A may have a thickness of around 1 inch at one side edge of the pillow and uniformly increasing to a thickness of around 2 inches at the other side edge.

Figure 6:
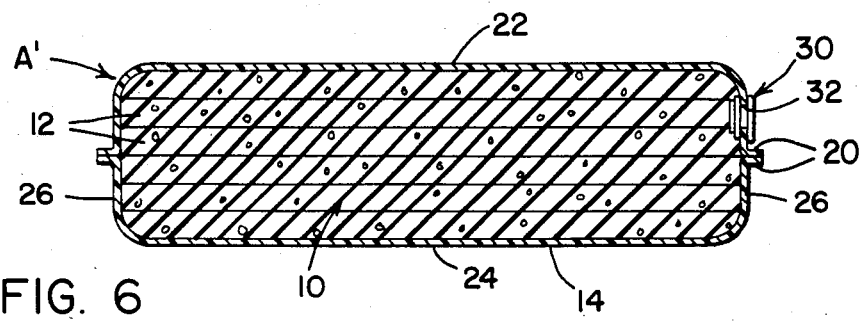
FIG. 6 is a transverse sectional view of a modified form of the surgical pillow.

Instead of tapering in thickness from one side edge to the opposite side edge, the surgical pillow comprising the invention may be of uniform thickness throughout as shown in the modified pillow A' illustrated in FIG. 6. The top and bottom surfaces 22, 24 of such a modified pillow A' then lie approximately parallel to one another.

Figure 8:
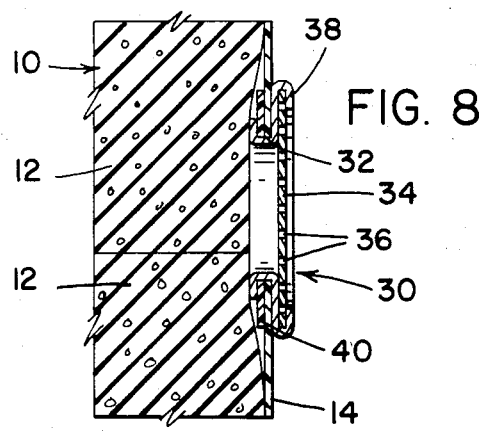

The envelope 14 is preferably open to the atmosphere but may be evacuated, if desired, in which case the plastic sheet material employed for the envelope should also be impervious to air and the envelope should be made air-tight following the insertion of the inner body or filler 10 thereinto. In the preferred form of the invention where the envelope 14 is open to the atmosphere, and particularly where the inner body member or filling 10 is of readily compressible or spongy character, the envelope is provided with a relatively small size vent means 30 for permitting release of entrapped air from the envelope on compression of the pillow and inflow of ambient air back into the envelope, on ensuing decompression of the pillow, to thereby cause self-restoration of the pillow to its original size and shape. By providing for forced air outflow from the pillow on compression, the vent means 30 thus prevents entrapped air or gas in the pillow from distorting the supported body organ and enables the pillow to readily accommodate itself to the contour of the portion of the patient's heart H or other organ to be supported thereagainst during operations thereon so that they are then held in a steady position at such time. As shown in FIGS. 6 and 8, the vent means 30 comprises an opening 32 in the side wall 26 of the envelope 14. In the case of the graduated thickness pillow A shown in FIG. 5, the vent means 30 is preferably located in that portion of the side wall 26 of the envelope 14 at the thicker end of the pillow so as to be exposed to the anterior side of the patient's heart H and face outwardly of the patient when the pillow is in use, as shown in FIGS. 1 and 2. Where the pillow is of uniform thickness throughout as in FIG. 6, the pillow A' may be formed of rectangular or square peripheral configuration in which case the vent means 30 is preferably located in a portion of the side wall 26 of the envelope 14 adjacent one or the other of the corners of the pillow.

As shown more particularly in FIG. 8, the vent opening 32 of the vent means 30 in the envelope 14 is covered by a thin perforated diaphragm 34 of a thin but relatively stiff plastic sheet material, or of a thin metal sheet material such as brass, and provided with a multiplicity of minute openings 36 therethrough communicating with the interior of the envelope 14 and through which air can flow either outwardly or inwardly of the envelope. The perforate diaphragm 34 is suitably fastened in place on the envelope 14 across the vent opening 32 therein as by means of a sealing clamp ring or fastening collar 38 suitably of brass which is secured to the diaphragm 34 as by clamping or clinching it around the periphery thereof and is also clamped to the material of the envelope 14 around the periphery of the vent opening 32 therein. The fastening of the clamp ring 38 and associated diaphragm 34 to the thin plastic sheet material of the envelope 14 may be strengthened or reinforced by the interposition therebetween of a thin stiffening collar or layer 40 of plastic or other suitable stiffening sheet material.

Figure 7:
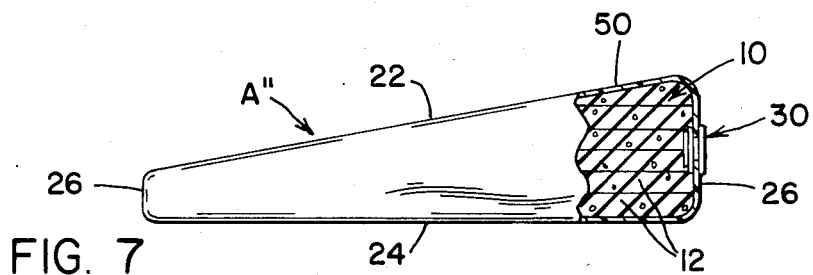
FIG. 7 is a view similar to FIG. 5 of another modified form of the surgical pillow; and, FIG. 8 is an enlarged partial sectional view, on the line 8—8 of FIG. 2, of the surgical pillow showing the detail of the air vent means thereof.

FIG. 7 illustrates a modified form A" of the pillow A shown in FIG. 5, wherein the envelope 50 is formed in one piece, instead of in two sections 16, 18 as in FIG. 5. In this modified pillow A", the one-piece envelope 50 may be provided with a longitudinal slit opening (not shown) along one of its side walls 26 through which the inner body 10 of spongelike cellular material may be introduced into the envelope, after which the slit opening may then be closed as by heat sealing the marginal edges of the slit opening together. Also in the modified pillow A" of FIG. 7, the vent means 30 for the envelope 50 may be located in the portion of the side wall 26 of the envelope at the thickest end thereof instead of being located closely adjacent the thickest end as in FIG. 5.

The surgical pillow A comprising the invention may be made in various sizes and peripheral contours, depending on the particular body organ to be supported in steady position during surgery. Thus, the pillow may be formed of approximately circular or oval peripheral contour as shown in FIGS. 1–5, or of approximately rectangular peripheral contour as in FIG. 6. For use as a heart support during bypass operations, a circular pillow A may have, for example, a diameter of around 6 to 7 inches and a thickness uniformly increasing from around ¾ inch at one side edge to around 1¼ inch at the opposite side edge for thin pillows, and around 1¼ inch at one side edge to around 2 inches at the opposite side edge for thick pillows. Rectangular pillows A' for use in heart bypass operations may have, for example, a length of around 7 inches and a width of around 5 inches, with a uniform thickness throughout of around 1¼ inches.

In the use of a surgical pillow A to support a patient's heart H as shown in FIGS. 1 and 2 during a bypass operation thereon, the apex portion of the heart is lifted slightly out of the surgically opened pericardial cavity of the patient and the pillow A then inserted between the heart and the diaphragm D and placed against the left and right ventricles Vl, Vr of the heart, with the thicker end of the pillow facing outwardly of the heart, whereupon the so positioned heart and pillow are then lowered back into the pericardial cavity of the patient with the pillow compressed between the heart and the patient's diaphragm D. During this pillow positioning step, the pillow A, because of its cushioning property and ability to release the air from the interior of the pillow envelope 14 through the vent means 30 thereof on compression of the pillow, will readily accommodate itself to the contour of the portion of the heart H engaged and pressed thereagainst so as to effectively support the heart in steady position for bypass operations thereon. Also, the non-skid exterior surface provided on the envelope 14 of the pillow in the preferred form of the invention assures against slippage of the heart or other body organs on the pillow during the course of surgical operations thereon. Most importantly, because of the relatively even surfaced exterior of the pillow A provided by the polyethylene outer envelope 14 thereof, and also because of its property of being nonabsorptive of blood, none of the patient's blood is absorbed by and need be recovered from the pillow during or after the bypass operation. As a consequence, little or no additional blood of the patient's blood type is required to be transfused into the patient's circulatory system during the bypass operation. The use of the surgical pillow comprising the invention thus greatly facilitates, and minimizes the time required for heart bypass and other body organ operations and reduces the expense thereof.

Figure 3:
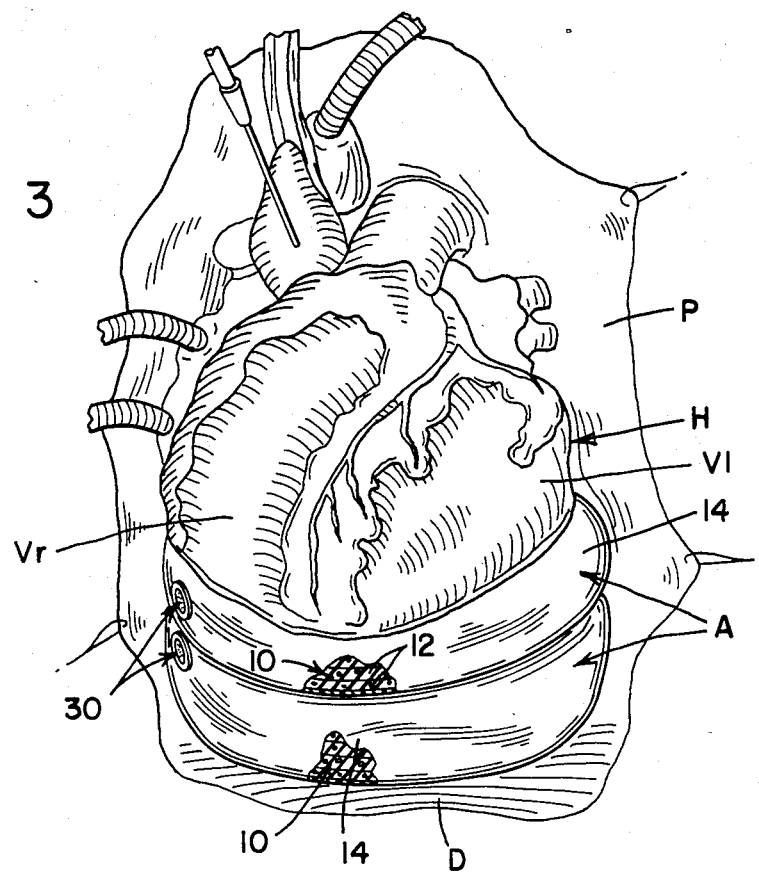
FIGS. 3 and 4 are views similar to FIGS. 1 and 2, respectively, but showing the heart of a patient supported by a stacked arrangement of a plurality of surgical pillows comprising the invention.
Figure 4:
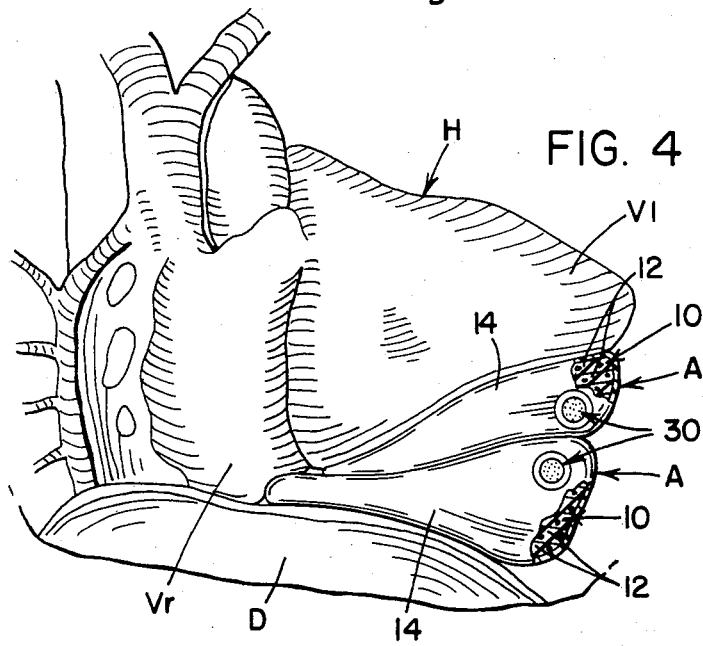

In cases where the patient's heart H is to be supported in a somewhat higher position in the pericardial cavity than is possible with a single pillow A comprising the invention, two or more of the pillows A may be stacked one next to another, with their thicker ends facing outwardly, to support the heart in such higher elevated position, as shown in FIGS. 3 and 4. Also in such case, one or more of the pillows A may have a greater thickness than the other or others, as illustrated in FIG. 4.

The invention has been described with reference to preferred embodiments thereof. Obviously, modifications and alterations will occur to others upon the reading and understanding of this specification. It is my intention to include all such modifications and alterations insofar as they come within the scope of the appended claims or the equivalents thereof.

Having thus described the invention, the following is claimed:

1. The method of performing open heart surgery on a patient including the step of lifting the heart from the pericardial cavity of the patient and then resting the heart against a surgical pillow of generally flat shape inserted between the heart and the diaphragm of the patient and comprised of an inner cushion filler formed of a material comprising one from the group consisting of an aggregate of foamed plastic particles or a foamed spongy body of aeriferous cellular plastic or rubber material completely enclosed and sealed within an envelope comprised of a thin flaccid synthetic plastic sheet material impervious to air and liquid and nonabsorbent of blood and provided with vent means in the side edge wall of the envelope for releasing entrapped air or gas from the pillow on compression thereof.

2. The method of performing open heart surgery on a patient including the step of lifting the heart from the pericardial cavity of the patient and then resting the heart against a surgical pillow of generally flat shape inserted between the heart and the diaphragm of the patient and readily accommodating itself to the shape of the portion of the heart resting thereagainst, said pillow comprised of an inner cushion filler formed of a material comprising one from the group consisting of an aggregate of foamed plastic particles or a foamed spongy body of aeriferous cellular plastic or rubber material completely enclosed and sealed within an envelope comprised of a thin flaccid synthetic plastic sheet material impervious to air and liquid and nonabsorbent of blood.

3. The method of performing organ surgery on a patient including the step of shifting the organ from its normal location in the patient and then holding the organ in its shifted position by a surgical pillow of generally flat shape inserted between the organ and an adjoining tissue portion of the patient and readily accommodating itself to the shape of the portion of the organ resting thereagainst, said pillow comprised of an inner cushion filler formed of a material comprising one from the group consisting of an aggregate of foamed plastic particles or a foamed spongy body of aeriferous cellular plastic or rubber material completely enclosed and sealed with an envelope comprised of a thin flaccid synthetic plastic sheet material impervious to air and liquid and nonabsorbent of blood.

* * * * *